US012754047B2

(12) United States Patent
Deutch

(10) Patent No.: US 12,754,047 B2
(45) Date of Patent: Oct. 6, 2026

(54) APPARATUS FOR MEASURING AND DISPLAYING THE IMPULSE OF A LIQUID STREAM

(71) Applicant: Adam J. Deutch, Olney, MD (US)

(72) Inventor: Adam J. Deutch, Olney, MD (US)

( * ) Notice: Subject to any disclaimer, the term of this patent is extended or adjusted under 35 U.S.C. 154(b) by 231 days.

(21) Appl. No.: 18/229,009

(22) Filed: Aug. 1, 2023

(65) Prior Publication Data

US 2024/0044681 A1 Feb. 8, 2024

Related U.S. Application Data

(60) Provisional application No. 63/395,199, filed on Aug. 4, 2022.

(51) Int. Cl.

*G01F 1/05* (2006.01)
*A61B 5/20* (2006.01)
*A63B 67/00* (2006.01)
*E03D 13/00* (2006.01)

(52) U.S. Cl.

CPC ................ *G01F 1/05* (2013.01); *A61B 5/208* (2013.01); *A63B 67/00* (2013.01); *A63B 2220/50* (2013.01); *A63F 2250/04* (2013.01); *E03D 13/005* (2013.01)

(58) Field of Classification Search

CPC ......... G01F 1/005; A63B 5/208; A63B 67/00; A63B 2220/50; A63F 2250/04; A63F 2250/58; E03D 13/005

See application file for complete search history.

(56) References Cited

U.S. PATENT DOCUMENTS

| | | | | |
|---|---|---|---|---|
| 6,385,796 | B1 * | 5/2002 | Muir, Jr. | E03D 13/00 4/304 |
| 9,550,115 | B2 * | 1/2017 | Silva | A47K 17/00 |
| 2008/0125293 | A1 * | 5/2008 | Ng | A63B 69/32 482/84 |
| 2013/0221618 | A1 * | 8/2013 | Freriks | F41J 5/04 273/371 |
| 2016/0181129 | A1 | 6/2016 | Dalmer et al. | |
| 2022/0016508 | A1 * | 1/2022 | Baer | A63B 71/0622 |

FOREIGN PATENT DOCUMENTS

CN 103292858 A * 9/2013

OTHER PUBLICATIONS

"Impulse (physics)" by Wikipedia, Feb. 13, 2022 https://en.wikipedia.org/windex.ph.?title=Impulse_(physics)&oldid=1-71608555 (Year: 2022).*

* cited by examiner

*Primary Examiner* — Justin N Olamit
(74) *Attorney, Agent, or Firm* — KARCESKI IP LAW, PLLC

(57) ABSTRACT

An apparatus for measuring and displaying an impulse value of a flowing liquid stream includes a force sensor adapted to be positioned within the flowing liquid stream. The force sensor relays a force value in response to an applied force of a flowing liquid stream. A controller is connected to the force sensor. The controller receives the force value from the force sensor, generates a time duration corresponding to the applied force of the flowing liquid stream, calculates an impulse from the force value and time duration, and generates an impulse value. A display is connected to the controller. The display receives the impulse value and displays a representation of the impulse value. A power source is connected to the force sensor, the controller, and the display to provide electrical power thereto.

10 Claims, 4 Drawing Sheets

300

```
#include <Wire.h>
#include <LiquidCrystal_I2C.h>
LiquidCrystal_I2C lcd(0x3F, 16, 2);
float previous = 0, current = 0;

void setup() {
  Serial.begin(115200);
  Serial.print(“The program is running”);
  lcd.begin();
  lcd.backlight();
  updateDisplay();
}

void loop() {
  float measurement = 0;
  while (measurement < 0.02) {
    int reading = analogRead(A0);
    float lbs = 0.00604581 × reading;
    measurement = lbs;
    delay(50);
  }
  Serial.println(“Weight detected.”);
  unsigned long lastValidValueTime = millis();
  while (millis() < lastValidValueTime + 5000) {
    int reading = analogRead(A0);
    float lbs = 0.00604581 × reading;
    if (lbs > 0.10) lastValidValueTime = millis();
    current = current + lbs × 0.20;
    updateDisplay();
    delay(200);
  }
  Serial.print(“Measurement over. Current: ”);
  Serial.println(current);
  previous = current;
  current = 0;
  updateDisplay();
}

void updateDisplay() {
  lcd.setCursor(0, 0);
  lcd.print(“Current:       ”);
  lcd.setCursor(9, 0);
  if (current == 0)
    lcd.print(“Ready”);
  else
    lcd.print(current);
  lcd.setCursor(0, 1);
  lcd.print(“Previous: ”);
  lcd.print(previous);
}
```

Figure 3

APPARATUS FOR MEASURING AND DISPLAYING THE IMPULSE OF A LIQUID STREAM

CROSS-REFERENCE TO RELATED APPLICATIONS

This United States Non-Provisional Patent Application relies for priority on and claims priority to U.S. Provisional Patent Application Ser. No. 63/395,199, filed on Aug. 4, 2022, the entire content of which is incorporated herein by reference.

FIELD OF THE INVENTION

The present invention addresses the correlation between varying forces with respect to time, which can be defined in simpler terms as impulse. More specifically, the invention relates to using electronic components to measure and display the impulse of a continuous liquid stream; that is, the calculated force and duration that a flowing liquid applies on or to a surface.

BACKGROUND OF THE INVENTION

It has been reported that 54% of adults regularly use their phones to play games. (See, e.g., Armstrong, M., & Richter, F., *Infographic: Smartphones Rule Gaming*, Statista Infographics, Jan. 26, 2022.)

Of the 85% of men who own a smartphone, 80% use it while in the bathroom, and 35% of the time it is for playing games. (See, e.g., Turner, A., *Texting On The Toilet, Cell Phone in Toilet Statistics* 2022, BankMyCell, 2022, Jan. 3, 2022.)

As such, there is interest in developing games that may be played during periods of bathroom use.

SUMMARY OF THE INVENTION

One contemplated use of the present invention is as a novelty in a bar/pub establishment, in a men's bathroom urinal.

By utilizing the present invention in an environment where intoxicated people seek engagement, the placement within a bathroom (specifically a men's room urinal) will provide stimulation and excitement among people as they try to "score" the highest.

According to an aspect of the present invention, there is provided an apparatus and a method for measuring and displaying the impulse of a flowing liquid stream.

The flowing liquid stream is contemplated to be a urine stream.

Among various non-limiting aspects, the apparatus includes a series of components that are linked and operate according to a set of criteria, details of which are set forth hereinbelow.

In one nonlimiting example, the present invention encompasses an apparatus for measuring and displaying an impulse value of a flowing liquid stream, such as a urine stream. The apparatus includes a force sensor adapted to be positioned within the flowing liquid stream. The force sensor relays a force value, in response to an applied force, of a flowing liquid stream. A controller is connected to the force sensor. The controller receives the force value from the force sensor, generates a time duration corresponding to the applied force of the flowing liquid stream, calculates an impulse from the force value and time duration, and generates an impulse value. A display is connected to the controller. The display receives the impulse value and displays a representation of the impulse value. A power source is connected to the force sensor, the controller, and the display to provide electrical power thereto.

In one contemplated example of the apparatus, the representation of the impulse value is a number.

In another contemplated example, the representation of the impulse value is non-numerical.

Still further, it is contemplated that the apparatus may be constructed such that the controller includes a processor on which a code is executed to generate the impulse value.

It is contemplated that the apparatus may also include a protective shield positioned between the force sensor and at least one of the controller, the display, and the battery.

In another contemplated example, two or more apparatuses may be linked together. The two or more apparatuses are contemplated to communicate and/or cooperate with one another.

The apparatus may also include a first communication link connecting the controller to the force sensor, a second communication link connecting the display to the controller, and a third communication link connecting the power source to the force sensor, the controller, and the display to provide electrical power thereto.

The first, second, and third communication links may be wired connections.

At least the first and second communication links may be wireless connections.

In one contemplated example, the force value is within a range between a minimum force value and a maximum force value.

The minimum force value may be within a range between approximately 0.001 and 0.100 lbf (0.004 and 0.445 N).

The maximum force value may be within a range between approximately 2.500 and 4.500 lbf (11.121 and 20.017 N).

It is contemplated that the applied force may be applied to the force sensor for a time duration separated into a plurality of time duration intervals, each of which is within a range between approximately 100 and 300 ms.

It is also contemplated, for another example of the apparatus, that the controller includes a clock to generate the plurality of time duration intervals.

It is also contemplated that the controller includes a processor that generates the impulse value from the force value and the plurality of time duration intervals.

In one contemplated example, the processor executes a programmable code to calculate the impulse value.

The apparatus may be configured so that the programmable code calculates the impulse value as the function of the force value and the time duration according to an equation:

$$J = \int_{t_1}^{t_2} F(t)dt$$

wherein "J" represents the calculated impulse, "F" represents the force, and "(t)dt" represents the integral with respect to the time duration over which the force acts, shown as "$t_1$", a starting time, and "$t_2$", an ending time.

These and other aspects, features, and characteristics of the present invention will become more apparent upon consideration of the following description and the claims with reference to the accompanying drawings, all of which form a part of this specification.

BRIEF DESCRIPTION OF THE DRAWINGS

The components of the following Figures are illustrated to emphasize the general principles of the present disclosure. It is to be expressly understood, however, that the drawings are for the purpose of illustration and description only and are not intended as a definition of the limits of the present invention.

FIG. 3 provides a sample code to function the apparatus depicted in FIGS. 2A and 2B, while also illustrating one approach for executing the logical progression presented in FIG. 1.

DETAILED DESCRIPTION OF THE INVENTION

Figure 1:
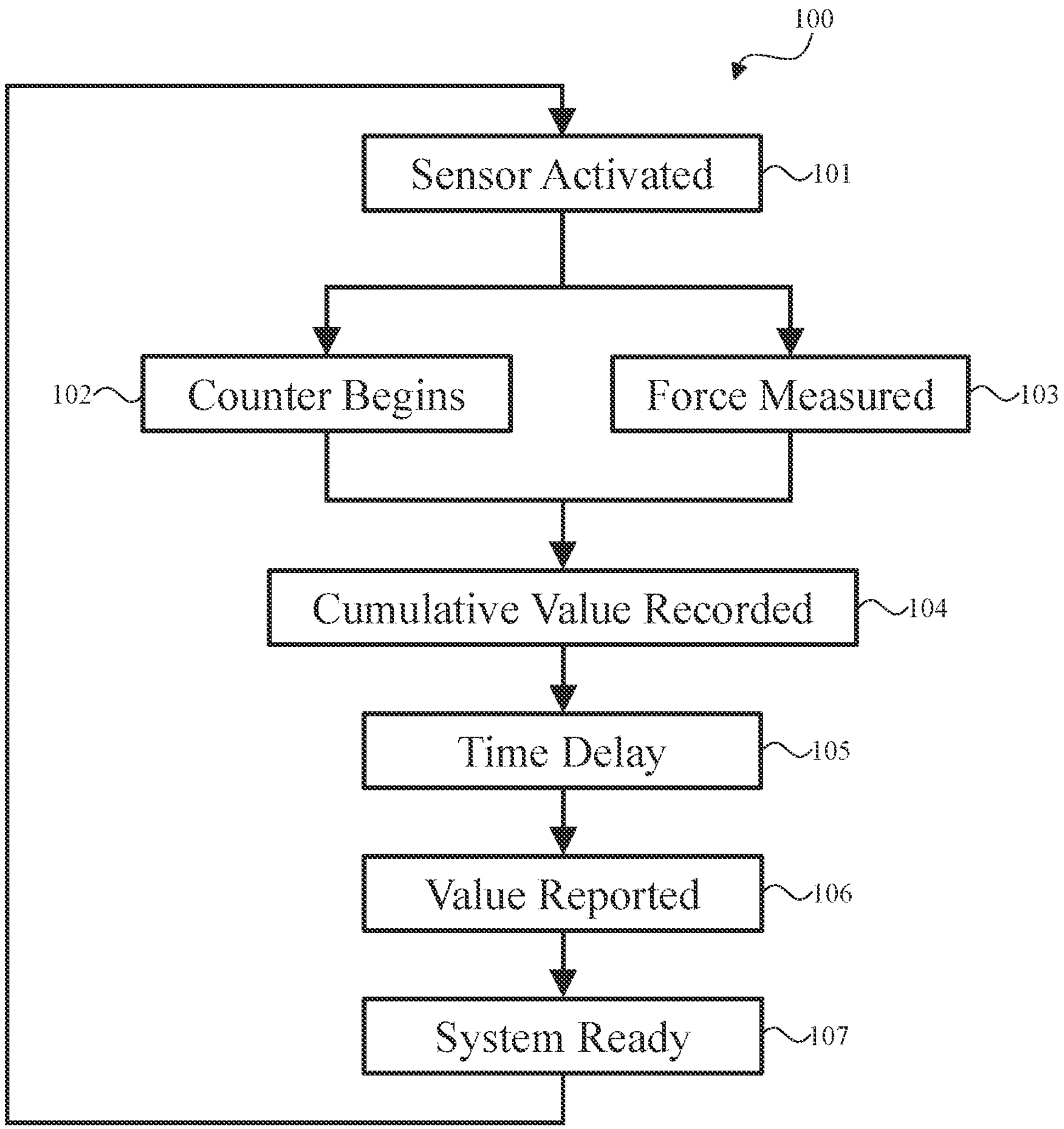
FIG. 1 graphically demonstrates a flow diagram, outlining a logical sequence contemplated by one embodiment of the present invention.

The terminology used herein is for the purpose of describing the particular embodiments only and is not intended to be limiting of the present invention. Any reference to the "present invention" is intended to refer to one or more embodiments contemplated for the present invention. As such, any discussion of the "present invention" is not intended to limit the present invention to any one embodiment described herein.

Use of the words "first," "second," "third," etc., is used to identify multiple components of the same type from each other. Use of the words "first," "second," "third," etc., is not intended to convey a hierarchy of components unless otherwise indicated.

As used herein, the term "and/or" includes any and all combinations of one or more of the associated listed items. As used herein, the singular forms "a," "an," and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs.

It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the present invention, it will be understood that a number of techniques and steps are disclosed. Each of these techniques and steps has individual benefits, and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the present invention and the claims.

A new method for calculating the impulse of a continuous liquid stream, an apparatus to accomplish this task, and a methodology for the execution of the device are discussed herein. In the following description, for the purposes of explanation, numerous specific details are set forth in order to provide a thorough understanding of the present invention. It will be evident, however, to one skilled in the art that the present invention may be practiced without these specific details.

The present disclosure is to be considered an exemplification of the present invention and is not intended to limit the present invention to the specific embodiments illustrated by the figures or description below.

By way of contextual background for the present invention, physics defines impulse as a force acting over time, which is also a change in momentum; an impulse is a force multiplied by the amount of time the force acts on an object.

Impulse can be calculated by taking the integral of force with respect to time, equal to the area under a force-time curve, as set forth in the equation below:

$$J = \int_{t_1}^{t_2} F(t)dt$$

wherein "J" represents the calculated impulse, "F" represents the force, and "(t)dt" represents the integral with respect to the time duration over which the force acts, shown as "$t_1$", a starting time, and "$t_2$", an ending time. When calculating impulse in increments, the trapezoidal rule states that smaller impulses over multiple time increments are summed together to determine the total area under a force-time curve.

Force is a vector quantity, which means that it has a magnitude and a direction.

Impulse is a vector quantity with the same direction as the force. Impulse is used to quantify the effect of a force acting over time to change the momentum of an object.

In the metric system of measurement (International System of Units, or SI), impulse, and therefore momentum, is measured in Newton-seconds (N×s), which is equivalent to the Joule (J), and kilogram-meters per second (kg×m/s).

The imperial system of measurement (United States Customary System Units, or USCS) most commonly calculates impulse in pound-seconds (lbf×s) and slug-feet per second (slug×ft/s).

Turning to one aspect of the present invention, FIG. 1 illustrates one example of a non-limiting logic progression 100 (also referred to as a "flow chart" or "flow diagram") contemplated for use by the present invention. As should be apparent to those skilled in the art, variations of the logic progression 100 may be employed without departing from the scope of the present invention.

To begin, a sensor, such as the force sensitive resistor 203 (illustrated in FIGS. 2A and 2B), is activated at step 101 through an applied force. Here, the applied force is the force of a liquid stream, such as a urine stream, impacting the force sensitive resistor 203.

Upon activation at step 101, two simultaneous events occur: (1) a clock initiates at step 102 to measure a time duration (e.g., a plurality of time duration intervals), and (2) the applied force is measured at step 103. In the example illustrated in FIG. 1, both the time duration and the force are continuously recorded at step 104 until a time delay is triggered at step 105. It is noted, however, that these two calculated variables need not be continuously recorded. One or both of the time duration and force may be recorded on a periodic basis without departing from the scope of the present invention.

At step 106, the programmable circuit board 202 (also referred to herein as a "controller 202") calculates and generates a reported output value. The reported output value is the calculated impulse. After the reported output value is generated, the logic progression advances to step 107, where the system re-initializes and prepares itself for a new trial.

Figure 2A:
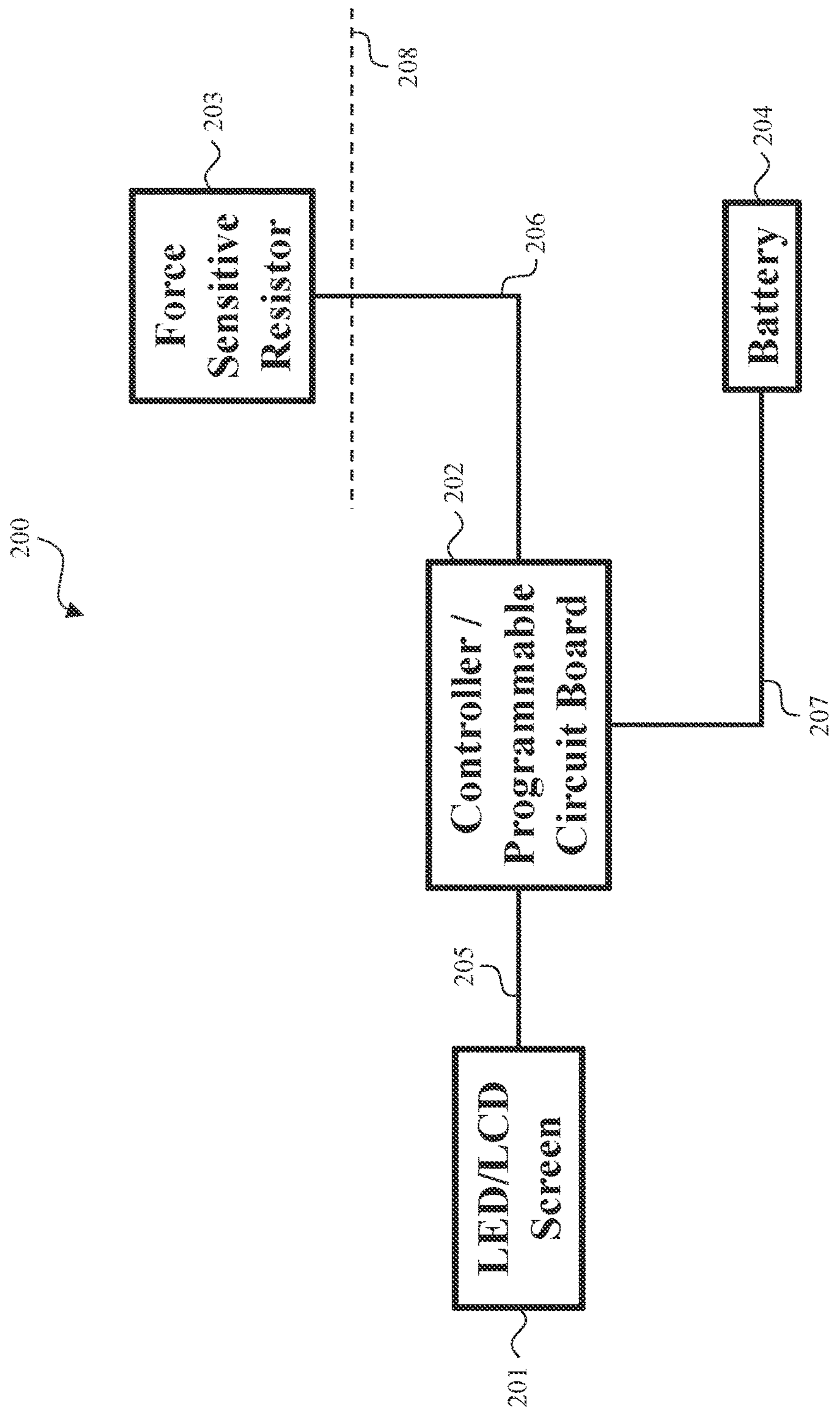
FIG. 2A is a diagram illustrating one contemplated arrangement of the relationships between the components for the apparatus of the present invention.
Figure 2B:
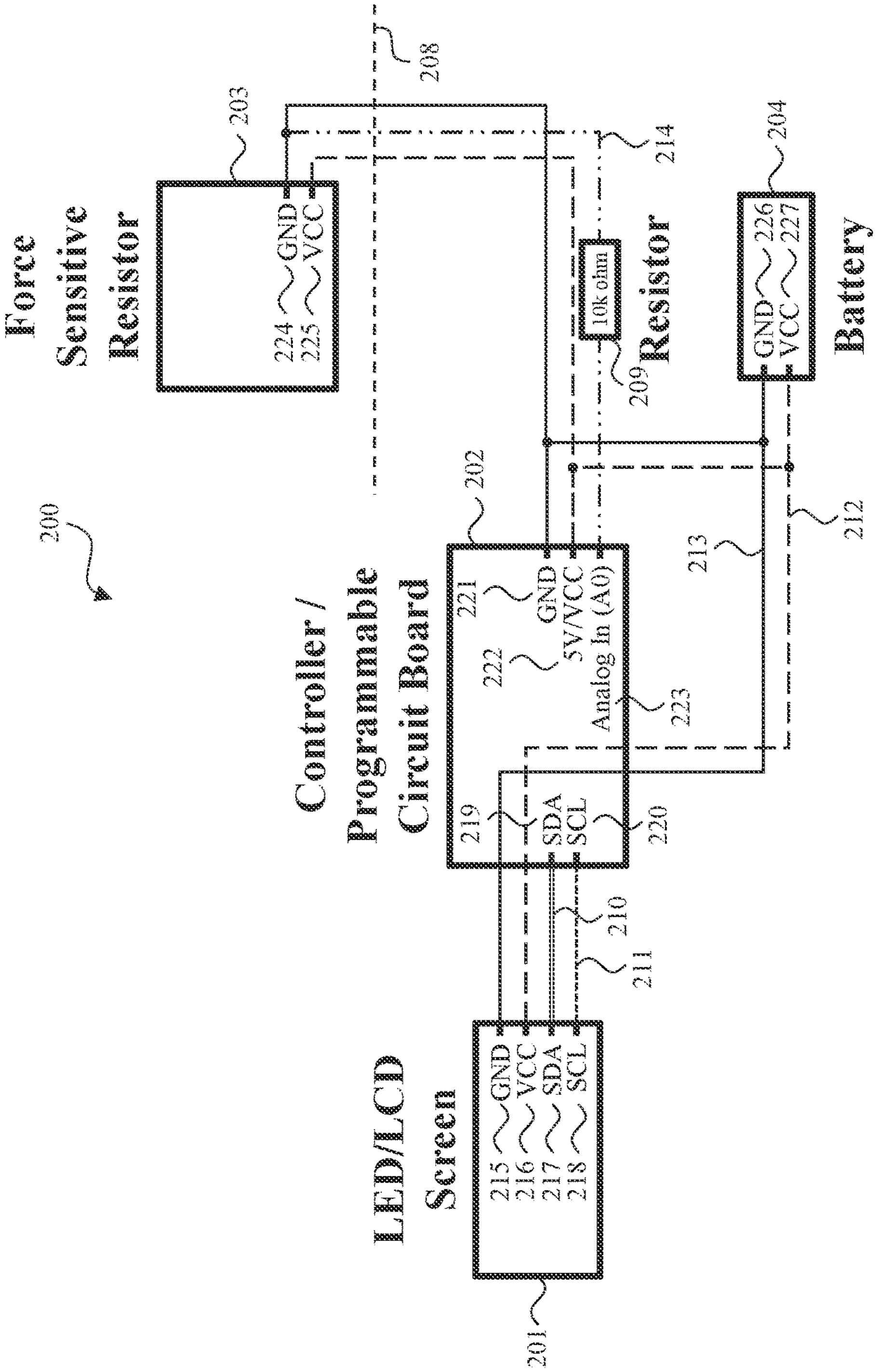
FIG. 2B is a circuit diagram and wiring schematic, based on the connections made in FIG. 2A, illustrating a second contemplated arrangement for the apparatus of the present invention.

As discussed, in connection with FIGS. 2A and 2B, the output value generated at step 106 is contemplated to be reported to a display 201, such as an LED/LCD screen 201. The display 201 presents the impulse value to the user.

In the context of a game connected to a urinal, the display 201 is contemplated to be located adjacent to the urinal so that the user can read the impulse value.

The present invention, however, also contemplates that the displays 201 for several urinals may be presented at a remote location, such as at the bar itself. Such a placement might be suitable if the bar establishes a contest between/among its patrons, for example. And, in connection with a competition, for example, several apparatuses 200 may be connected together to communicate and/or cooperate with one another.

It is noted that the present invention is contemplated to be employed primarily for men. However, the present invention may be employed for female users as well.

FIG. 2A illustrates a non-limiting arrangement of the different components utilized and the necessary connections for the apparatus 200 to operate according to an embodiment of the present invention.

The controller 202 is capable of executing the necessary computations and logic progression 100 illustrated in FIG. 1. The controller 202 incorporates a programmable circuit board and/or processor that executes the program illustrated in FIG. 1 (the code illustrated in FIG. 3) and performs the calculations required for operation of the apparatus 200. For this reason, the controller 202 is also referred to herein as a "programmable circuit board 202."

The programmable circuit board 202 may be an Arduino UNO REV 3, manufactured by Arduino, having a business address in Somerville, Massachusetts, USA. As should be apparent to those skilled in the art, however, any other programmable circuit board 202 may be employed without departing from the scope of the present invention.

There are three (3) components connected to the programmable circuit board 202: (1) a force sensitive resistor 203 (also referred to herein as a "force sensor 203"), (2) an LED/LCD screen 201 (also referred to herein as a "display 201"), and (3) a battery source 204 (also referred to herein as a "battery 204").

A simplistic, graphical diagram of the apparatus 200 components is provided in FIG. 2A. As shown, the force sensor 203 is connected to the controller 202 via a one-way connection 206 that feeds user input data, in the form of an applied force, into the controller 202. This connection is also referred to herein as a "first communication link." The input data is generated by the force sensor 203 as a measurement of the force applied from the user. The force is contemplated to be within a range of 0.001 and 4.500 lbf (pounds-force), or 0.004 and 20.017 N (Newtons), with values between 0.020 and 3.500 lbf (0.089 and 15.569 N) being considered as defining a suitable range for the present invention. The duration of the applied force is contemplated to be within a range of 1 and 60 seconds. The force sensor 203 is contemplated to be a resistive element. However, other force sensors may be employed without departing from the scope of the present invention.

The display 201 is connected to the controller 202 via an open-drain driver and connection 205 that outputs a value onto the display 201. In a non-limiting example, the display 201 may be a 1602 16×2 Serial LCD Display Module, for example. The connection between the display 201 and the controller 202 is also referred to herein as a "second communication link."

The battery 204 is connected to each of the previously stated components via a one-way connection that provides power to the entire apparatus 200. The battery 204 may be a standard 9V battery, for example. This connection is also referred to herein as a "third communication link."

FIG. 2B illustrates, in greater detail, the relationships between the non-limiting components illustrated in FIG. 2A according to an embodiment of the present invention.

As previously stated, the apparatus 200 is controlled by a programmable circuit board 202 that is connected to three (3) components: (1) a force sensitive resistor 203, (2) an LED/LCD screen 201, and (3) a battery source 204.

The controller 202 utilizes five (5) connection points: (1) a power input pin (5V/VCC) 222, (2) a ground pin (GND) 221, (3) an Analog In (A0) pin 223, (4) an SDA pin (serial data) 219, and (5) an SCL pin (serial clock) 220.

The force sensitive resistor 203 utilizes two (2) connection points: (1) a power input pin (VCC) 225 and (2) a ground pin (GND) 224.

The LED/LCD screen 201 utilizes four (4) connection points: (1) a power input pin (VCC) 216, (2) a ground pin (GND) 215, (3) an SDA pin (serial data) 217, and (4) an SCL pin (serial clock) 218.

The battery source 204 utilizes two (2) connection points: (1) a power input pin (VCC) 227 and (2) a ground pin (GND) 226.

Across the apparatus 200, the power input pins (VCC) 222, 225, 216, 227 are connected, via communication link 212, to provide power to each component. The ground pins (GND) 221, 224, 215, 226 are connected, via communication link 213, due to the fact that all electrical components must be "grounded" in order to complete a circuit. Additionally, the ground pin (GND) 224 on the force sensor 203 is connected, via communication link 214, to the Analog In (A0) pin 223 on the controller 202, which allows the data input from the force sensor 203 to be received by the controller 202. To regulate the flow of electrical current, a 10 kΩ (kiloohm) resistor 209 is required, within communication link 214, per the specifications of the non-limiting thin film pressure force sensor 203.

It is noted that the 10 kΩ resistor 209 is specific to the embodiment illustrated. Other embodiments are contemplated to require a resistor 209 with a different resistance. Still further, it is contemplated that no resistor 209 may be needed in some possible embodiments of the present invention.

The controller 202 sends and receives data to the display 201 via SCL pins 218, 220 and communication link 211, and through SDA pins 217, 219 and communication link 210; "SCL" is the serial clock pin that the controller 202 pulses at a regular interval, and "SDA" is the serial data pin over which data is sent between the two components.

In one contemplated embodiment, the communication links 205, 206, 207 are wired links. However, any one or all of the communication links 205, 206, 207 may be wireless links. If wireless communication links 205, 206, 207 are employed, the controller 202 may be positioned remotely with respect to the remaining components of the apparatus 200, for example. The only communication link that may be wired is the link between the battery 204 and the controller 202.

Still further, it is contemplated that two or more of the apparatuses 200 may be connected to one another. When two or more apparatuses 200 are connected, it becomes possible for users to compete with one another, for example.

While FIG. 2B illustrates one contemplated arrangement for the display 201, the controller 202, the force sensor 203, and the battery 204, those skilled in the art will recognize that other components may be employed without departing from the scope of the present invention.

The operation of the apparatus 200 will now be described in connection with the code 300 illustrated in FIG. 3.

As noted above, the code 300 is contemplated to be executed on a processor that is a part of and/or embodied in the controller 202. The code 300 is contemplated to be stored in memory (volatile or nonvolatile) connected to the processor. Alternatively, as noted, the code 300 may be hard-wired as a function of one or more circuit elements comprising the controller 202. The construction of the controller 202 is within the knowledge of those skilled in the art and, therefore, is not elaborated upon here.

Before delving into the specifics of the code 300, a brief overview of the operation of the apparatus 200 is provided. Specifically, the apparatus 200 operates as follows. When a fluid stream impacts the force sensor 203, it generates an electronic signal, referred to herein as a "force value." The force value is relayed, as an input, into the controller 202. The controller 202 calculates an impulse, as an output, using the force value and duration over which it acts as inputs. Duration is determined via a counter resident in or on the controller 202. The impulse value, which is also an electronic signal, is provided to the user on the display 201.

With this simplified overview of the operation of the apparatus 200, a more detailed discussion is provided in connection with the implementation/example illustrated as the code 300 in FIG. 3.

FIG. 3 demonstrates a non-limiting code 300 that supports FIGS. 1, 2A, and 2B according to an embodiment of the present invention. The code 300 is contemplated to be uploaded to the controller 202 to operate the apparatus 200. Alternatively, it is contemplated that hardware may be configured to implement part or all of the code 300 described below.

While specific aspects of the implementation of the code 300 are discussed herein, the present invention should not be understood to be limited solely to the code 300 described and illustrated herein. Variations of the code 300 may be implemented without departing from the scope of the present invention.

Lines 301 and 302 set up the code 300 and pull specific coding directories into the operation of the code 300. Line 303 defines the format of the information on the display 201, and Line 304 declares the two values being calculated as floating-point numbers, meaning they have a decimal point. The setup in Line 306 means that the commands in Lines 307 through 312 are executed only once and serve two main points: to define the serial monitor, which acts as a tie between the originating computer setup and the controller 202, and to trigger the display 201 that the apparatus 200 is being used to power.

Lines 314 through 337 act as the main body of the non-limiting code 300. In order to calculate the impulse being imparted by a fluid stream, the force sensor 203 must be triggered, as indicated at step 101, by an applied force. The applied force is provided by a fluid stream. The code 300 will not initiate or alter from the previous setup command, as indicated in Lines 306 through 312, until the force sensor 203 is triggered by a force greater than the value stated in Line 316, which the loop in Line 314 searches for in increments of the value in Line 320, in milliseconds. In the illustrated example, the minimum force is set to 0.020 lbf, which is also 0.089 N. In the code 300 illustrated in FIG. 3, the time delay increment to search for the initiating value is 50 ms (milliseconds). In other words, in order for a trial to begin, the code 300 searches for a minimum applied force of 0.020 lbf every 50 ms on the force sensor 203.

As should be apparent to those skilled in the art, the minimum force of 0.020 lbf and the time increment of 50 ms are merely exemplary of the values that the code 300 may employ. Other values may be employed without departing from the scope of the present invention. For example, the minimum force may be defined by a range between 0.001 and 0.100 lbf (0.004 and 0.445 N), or 0.010 and 0.050 lbf (0.045 and 0.222 N), with 0.020 lbf (0.089 N) or 0.25 lbf (1.112 N) being selected as average parameters. Similarly, the time delay increment of 50 ms may be varied within a range between 1 and 100 ms, 25 and 75 ms, or 40 and 60 ms without departing from the scope of the present invention, for example.

A maximum triggering force may also be set so that the code 300 does not interpret unreasonably large values, for the typical force of a fluid/urine stream, and can avoid instances where a person might cheat while playing a game, as defined herein. A range for the maximum force may be set between 2.500 and 4.500 lbf (11.121 and 20.017 N), or between 3.000 and 4.000 lbf (13.345 and 17.793 N), for example. By incorporating a maximum force value, the code 300 may be set to ignore clearly erroneous data that might be generated if a person presses on the force sensor 203 with their finger, for example.

Once an applied force is detected (step 101), Lines 322 and 323 are activated and two things occur simultaneously; (1) a time counter (step 102) initiates, and (2) the applied force is measured (step 103).

The time counter (step 102) abides by the value in the inequality in Line 324, in milliseconds, as well as the inequality in Line 327. This grouping says that, once a force less than the value in the inequality in Line 327, in pounds, is continuously observed for the duration defined in Line 324, in milliseconds, the trial is complete. Here, the minimum force value needed for a trial to complete is 0.100 lbf (0.445 N). The delay duration is 5000 ms (5 seconds). As should be apparent, this section of the code 300 determines that the fluid stream has ended by measuring the fluid stream force over an enumerated duration.

Here, the duration need not be set to 5000 ms. The duration may vary within a range between 1 and 10,000 ms, for example. Other contemplated durations include ranges between 1,000 and 9,000 ms, 2,000 and 8,000 ms, 3,000 and 7,000 ms, or 4,000 and 6,000 ms. Still other durations may be employed without departing from the scope of the present invention.

Similarly, the minimum force to complete a trial may vary from 0.100 lbf without departing from the scope of the present invention. Ranges for the minimum force to complete a trial may be set between 0.050 and 0.150 lbf (0.222 and 0.667 N), or 0.075 and 0.125 lbf (0.334 and 0.556 N), for example.

The measured force of the fluid stream, during the trial, is the second variable required to calculate impulse, defined by the equations in Lines 326 and 328. Once the force sensor 203 is activated (step 101), Line 325 instructs the force sensor 203 to send the data (e.g., the force value) to the Analog In (A0) pin 223 on the controller 202. The constant shown in Line 326 is determined by calibrating the force sensor 203 by using a line of best fit model to define the correlation between what the sensor reads and a preferable unit quantity; the precision in the constant increases the accuracy of the calibration. Here, the constant is 0.00604581.

As should be apparent, this constant has been selected for the force sensor 203 identified hereinabove. Other constants, selected for other force sensors, may be employed without departing from the scope of the present invention.

In solving for impulse (e.g., the impulse value), the integral of a force-time curve is equal to force multiplied by the duration over which the force acts, per the equation identified hereinabove. For the purposes of the present invention, a method most similar to the Trapezoidal Rule in Calculus is applied. This method states that an integral can be solved by dividing the area under a curve into multiple trapezoidal shapes. Line 328 demonstrates this principle with a trapezoidal height, equal to the frequency at which the force sensor 203 measures the applied force. This trapezoidal height, represented as a fraction of a second, is equal to Line 330 in that Line 330 states how often the force sensor 203 is measured, in milliseconds. Here, the time interval is 200 ms (0.20 seconds).

Naturally, the time interval may be varied from 200 ms without departing from the scope of the present invention. Ranges for the time interval may be set to between 100 and 300 ms or 150 and 250 ms, for example.

To calculate an impulse, per the equation identified hereinabove, the previously explained time interval is multiplied by the measured force at each of the time intervals. The function runs in a loop, per Line 324, continuously and cumulatively adding the calculated impulses 104, until the applied force falls below the specified inequality in Line 327 for a duration longer than the constant, in milliseconds, in Line 324, triggering a time delay (step 105). Here, as noted above, the minimum force to trigger a time delay is 0.100 lbf for a duration of 5000 ms.

Once a time delay is prompted (step 105), the code 300 instructs the display 201 to display/print the calculated impulse (step 106), and lines 332 through 336 are activated. Lines 339 through 350 define what characters and values to print on the display 201, as well as how to update those values for future trials. The characters include, but are not limited to, "Current:", "Ready:", and "Previous:".

Before a trial begins, the display 201 presents two (2) lines of text per Lines 341 and 348; on the display 201, the top line represents the current impulse value and the bottom line represents the previous impulse value. In the contemplated example, the impulse values are displayed as a numerical representation (or number) in units of N×s (Newton-seconds), kg×m/s (kilogram-meters per second), lbf×s (pound-seconds), or slug×ft/s (slug-feet per second), for example. In the alternative, the impulse values may be presented on the display 201 with a non-numeric representation. Therefore, the present invention is contemplated to encompass displays of both numeric and non-numeric representations (generically referred to as "representations") of the impulse values.

As noted, the display 201 need not be an LED/LCD screen. Instead, the display 201 may be a full color display, such as a television screen or computer monitor, for example. In such instances, graphical representations and/or illustrations may be provided to indicate the magnitude of the impulse values. Other information may also be provided, as desired.

Between trials, when no force is being applied to the force sensor 203 and the code 300 is running the loop in Lines 314 through 321, the display 201 follows Lines 340 through 344, reminding the user that the apparatus is ready to be used again (step 107). Here, no representations may be presented to the user.

Similarly, the bottom line on the display 201 follows Lines 347 through 349 and does not report a value because there is no previous value to display until a second trial begins. While the apparatus 200 is in use, the calculated impulse value is constantly updated and shown on the top line of the display 201 per Line 346. After the trial has concluded, the reported value (step 106) from the current trial, moves from the top line of the display 201 to the bottom line of the display 201 and follows Lines 347 through 349, once again alerting the user that the apparatus is ready for a new trial (step 107).

Since the apparatus 200 is contemplated to measure the impulse of a fluid/urine stream where liquids are present, it is contemplated that a protective shield 208 may be positioned to separate the force sensor 203 from the display 201, the programmable circuit board 202, the battery 204, and the source of the fluid/urine stream.

While preferred materials for elements have been described, the device is not limited by these materials. Wood, plastics, rubber, foam, metal alloys, aluminum, and other materials may comprise some or all of the elements of the impulse-calculating device and apparatuses in various embodiments of the present invention.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An apparatus for measuring and displaying an impulse value of a flowing liquid stream, comprising:

a force sensor adapted to be positioned within the flowing liquid stream, wherein the force sensor relays a force value in response to an applied force of the flowing liquid stream;

a controller connected to the force sensor, wherein the controller receives the force value from the force sensor, generates a time duration corresponding to the applied force of the flowing liquid stream, calculates an impulse as a function of the force value multiplied by the time duration, and generates an impulse value;

a display connected to the controller, wherein the display receives the impulse value and displays a representation of the impulse value;

a power source connected to the force sensor, the controller, and the display to provide electrical power thereto; and a clock associated with the controller to generate the time duration and to generate a plurality of time duration intervals, wherein the force value is within a range between a minimum force value and a maximum force value, wherein the controller initiates operation of the apparatus in response to receiving the minimum force value, wherein the minimum force value is within a range between approximately 0.001 and 0.100 lbf (0.004 and 0.445 N), wherein the controller limits operation of the apparatus in response to receiving the maximum force value, wherein the maximum force value is within a range between approximately 2.500 and 4.500 lbf (11.121 and 20.017 N), wherein the applied force is applied to the force sensor for the time duration separated into the plurality of time duration intervals, wherein each of the plurality of time duration intervals is within a range between approximately 100 and 300 ms, and wherein the controller comprises a processor that generates the impulse value from the force value and the plurality of time duration intervals.

2. The apparatus according to claim 1, wherein the representation of the impulse value is a number.

3. The apparatus according to claim 1, wherein the representation of the impulse value is non-numerical.

4. The apparatus according to claim 1, wherein:

the controller includes a processor on which a code is executed to generate the impulse value.

5. The apparatus according to claim 1, further comprising:

a protective shield positioned between the force sensor and at least one of the controller, the display, and the power source.

6. The apparatus according to claim 1, further comprising:

a second force sensor adapted to be positioned within a second flowing liquid stream, wherein the second force sensor relays a second force value in response to a second applied force of the second flowing liquid stream;

a second controller connected to the second force sensor, wherein the second controller receives the second force value from the second force sensor, generates a second time duration corresponding to the second applied force of the second flowing liquid stream, calculates a second impulse as a function of the second force value multiplied by the second time duration, and generates a second impulse value;

a second display connected to the second controller, wherein the second display receives the second impulse value and displays a representation of the second impulse value;

a second power source connected to the second force sensor, the second controller, and the second display to provide electrical power thereto; and a second clock associated with the second controller to generate the second time duration and to generate a second plurality of time duration intervals, wherein the second force value is within a range between the minimum force value and the maximum force value, wherein the second controller initiates operation of the apparatus in response to receiving the minimum force value, wherein the second controller limits operation of the apparatus in response to receiving the maximum force value, wherein the second applied force is applied to the second force sensor for a time duration separated into the second plurality of time duration intervals, wherein each of the second plurality of time duration intervals is within a range between approximately 100 and 300 ms, and wherein the second controller comprises a second processor that generates the second impulse value from the second force value and the second plurality of time duration intervals, and wherein a result of a competition is established by comparing at least the first impulse value with the second impulse value.

7. The apparatus according to claim 1, further comprising:

a first communication link connecting the controller to the force sensor;

a second communication link connecting the display to the controller; and a third communication link connecting the power source to the force sensor, the controller, and the display to provide electrical power thereto.

8. The apparatus according to claim 7, wherein the first, second, and third communication links are wired connections.

9. The apparatus according to claim 7, wherein at least the first and second communication links are wireless connections.

10. The apparatus according to claim 1, wherein the processor executes a programmable code to calculate the impulse value.

* * * * *